United States Patent [19]

Sieja

[11] Patent Number: 5,162,567
[45] Date of Patent: Nov. 10, 1992

[54] PURIFICATION OF 6-AMINOCAPRONITRILE

[75] Inventor: James B. Sieja, Wilmington, Del.

[73] Assignee: E. I. Du Pont de Nemours and Company, Wilmington, Del.

[21] Appl. No.: 841,351

[22] Filed: Feb. 27, 1992

[51] Int. Cl.$^5$ .......................................... C07C 253/34
[52] U.S. Cl. ...................................... 558/452; 203/29; 203/30; 203/38; 558/435; 558/454; 558/456
[58] Field of Search ................. 558/435, 452, 454, 456

[56] References Cited

U.S. PATENT DOCUMENTS

| | | | |
|---|---|---|---|
| 2,242,309 | 5/1941 | Lazier et al. | 558/456 |
| 3,004,059 | 10/1961 | Wüst | 558/452 |
| 3,177,242 | 4/1965 | Adam et al. | 558/456 |

FOREIGN PATENT DOCUMENTS

| | | | |
|---|---|---|---|
| 601619 | 7/1960 | Canada | 558/452 |
| 43-4494 | 2/1968 | Japan | 558/452 |
| 45-12849 | 5/1970 | Japan | 558/452 |

*Primary Examiner*—Joseph Paul Brust
*Attorney, Agent, or Firm*—Earl L. Handley

[57] ABSTRACT

Purification of 6-aminocapronitrile by heating a mixture containing same and THA and converting the THA to higher boiling compounds, and then distilling the 6-aminocapronitrile. The time required to convert the THA is reduced if an organic carbonyl compound is present in the mixture during heating.

8 Claims, No Drawings

PURIFICATION OF 6-AMINOCAPRONITRILE

FIELD OF THE INVENTION

This invention relates to the preparation of purified 6-aminocapronitrile from a mixture containing tetrahydroazepine (THA) by converting the THA to higher boiling compounds and then recovering 6-aminocapronitrile by controlled distillation. The 6-aminocapronitrile is then sufficiently pure to be polymerized to a high molecular weight 6-nylon having good color and low gel content.

BACKGROUND OF THE INVENTION

The polymerization of 6-aminocapronitrile to form nylon polymer is disclosed in Greenewalt U.S. Pat. No. 2,245,129 and Curatolo et al. U.S. Pat. No. 4,568,736.

When 6-aminocapronitrile is produced by partial hydrogenation of adiponitrile, hexamethylenediamine and tetrahydroazepine, i.e., the latter compound represented by the formula:

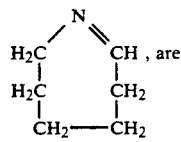

, are also coproduced. The hexamethylenediamine is easily removed from the mixture by simple distillation, but the tetrahydroazepine (hereinafter sometimes referred to as THA) is not easily separated. The presence of THA in the 6-aminocapronitrile (hereinafter sometimes referred to as 6-ACN) that is to be polymerized limits the molecular weight of the polymer and causes color and branching in the polymer. It is, therefore important that THA be removed from the 6-ACN before polymerization.

It is an object of the present invention to provide a simple and efficient method of obtaining 6-ACN that is free from THA.

It has now been found that by heating, 6-ACN to about 235 degrees C (approximately the atmospheric pressure boiling point of 6-ACN) the contained THA is slowly converted to compounds which can be separated from 6-ACN by simple distillation. Certain organic compounds can be added to the 6-ACN to reduce the time required to convert the THA.

SUMMARY OF THE INVENTION

The present invention is a process for the recovery of 6-aminocapronitrile from a mixture containing 6-aminocapronitrile and tetrahydroazepine which comprises (a) heating said mixture at a temperature of about 235 degrees C. to convert tetrahydroazepine to higher boiling compounds, and (b) then distilling the 6-aminocapronitrile from the resulting mixture. The presence of certain organic compounds in the mixture increases the speed at which the tetrahydroazepine is converted. Suitable organic compounds are compounds that will react with 6-ACN to from an imine. These imines are thermally unstable, and their by-products react with THA preferentially. Such compounds usually contain carbonyl groups: ketones and aldehydes. The amount of organic compound is preferably about 0.1 to 10% by weight of the initial mixture.

DETAILED DESCRIPTION

Temperature: Temperatures higher and lower than the normal boiling point of 6-aminocapronitrile can be used. Lower temperatures limit the rate of THA decomposition, and higher temperatures require pressure equipment, but would increase the rate of decomposition. The normal boiling point of 6-aminocapronitrile is preferred for convenience and practicality.

Organic Compound: Suitable compounds are organic carbonyl containing compounds that react with 6-ACN to from imines. Aldehydes and ketones and their derivatives such as oximes and hydrazones are satisfactory. Cyclopentanone and 5-formylvaleronitrile are preferred because of rate and completeness of reaction. They have the advantage of also being the by-products of 6-aminocapronitrile thermal decomposition, and hence do not introduce foreign materials into the 6-aminocapronitrile. Other suitable compounds include: methyl ethyl ketone, aceto-phenone, hexanal, and cyclohexanone.

An industrial process could be run in a batch or continuous mode. A batch cycle would involve addition of about 3-5% of a catalyst (e.g., cyclopentanone), distillation of the small amount of water which forms from the reaction of cyclopentanone with the 6-aminocapronitrile, heating for a period of about 2 hours at the normal boiling point of 6-aminocapronitrile, and then distillation of the THA-free 6-aminocapronitrile.

A continuous process would operate similarly. The 6-aminocapronitrile would have a residence time of approximately 2 hours at the normal boiling point of 6-aminocapronitrile. A fractionating column would continuously separate the low boilers and high boilers from the purified 6-aminocapronitrile.

DETAILED EXAMPLES

EXAMPLE 1

50 ml of 6-aminocapronitrile containing 0.19% of THA was refluxed (boiling point 235 degrees C.) for four hours. At this time the THA analyzed for 0.082%. 0.4 g (0.9 wt. %) of cyclopentanone were added, and refluxing was continued. After an additional 2.5 hours, the THA was reduced to <0.005%.

EXAMPLE 2

300 ml of 6-aminocapronitrile containing 0.23% THA were mixed with 300 ml of 6-aminocapronitrile distillation heels. The heels contain the imines of cyclopentanone and 2-methyl cyclopentanone. The THA level of the mixture was 0.38%. After refluxing for 6.5 hours, the THA measured 0.13%. After 22.5 hours, it measured 0.023%. Partial distillation gave 6-aminocapronitrile which contained 0.04% THA. The pot was then refluxed for 15 more hours, and the 6-aminocapronitrile was distilled to give 6-aminocapronitrile with <0.005% THA.

EXAMPLE 3

9 g of 6-aminocapronitrile containing 0.24% THA and 0.6 g of 5-formylvaleronitrile were refluxed. After 15 minutes the THA analyzed for 0.084%. After an hour, the THA was completely gone (<0.005%). 6-aminocapronitrile without the 5-formylvaleronitrile still contained 0.21% of THA even after one hour at reflux.

EXAMPLE 4

A mixture of 6.3 g of cyclopentanone and 633 g of 6-aminocapronitrile containing 0.5% THA was refluxed for 28 hours. The small amount of water formed by reaction of cyclopentanone with 6-aminocapronitrile was removed by distillation at the outset. After 7.5 hours at reflux, the THA measured 0.17%. After 23.5 hours, it measured 0.027%. At the end of 28 hours, it was less than 0.005%. The 6-aminocapronitrile was distilled at 0.25 mm mercury to give 6-aminocapronitrile with <0.005% THA.

Control for Example 5

A sample of 6-aminocapronitrile used in Example 4 (without added cyclopentanone) was distilled at 0.25 mm mercury. The distillate contained 0.22% THA. This shows that simple distillation without prior heat treatment does not eliminate the THA.

EXAMPLE 5

A mixture of 50 g of cyclopentanone and 1000 g 6-aminocapronitrile containing 0.27% THA was refluxed for 2 hours. The small amount of water from the reaction of the cyclopentanone and 6-aminocapronitrile was removed by distillation at the outset. The THA measured after 1 hr. was 0.01%, after 2 hours <0.005%. The mixture was distilled at 40 mm mercury to give THA-free 6-aminocapronitrile.

Control for Example 5

A sample of 6-aminocapronitrile used for Example 5 was refluxed for 4 hours. The THA measured 0.22%.

Examples 6-12—Series Using Other Promoters

Control containing no additives, cyclopentanone, methyl ethyl ketone, acetophenone, hexanal, cyclohexanone, 5-formylvaleronitrile.

Example 6—Control for Series 100 g of 6-aminocapronitrile containing 0.32% THA were refluxed for 30 hours. Samples were taken at 0, 1, 3, 5, 6.5, 22, 25, 30 hours, (the 0 sample was taken when the 6-aminocapronitrile started to reflux). The THA measured at these times was 0.32, 0.26, 0.28, 0.26, 0.26, 0.19, 0.18, 0.17%.

Example 7—Cyclopentanone

A mixture of 97 g of 6-aminocapronitrile containing 0.32% THA and 3 g of cyclopentanone was refluxed, and samples were taken at 0, 1, 2, 3, and 4 hours. The 0 hr. sample was obtained after distillation of the small amount of water which formed by the reaction of 6-aminocapronitrile and cyclopentanone, and the pot temperature rose to the boiling point of 6-aminocapronitrile. THA at these times measured, 0.06, 0.03, 0.01, 0.01, 0.001%.

Example 8—Methyl Ethyl Ketone

A mixture of 97 g of 6-aminocapronitrile containing 0.32% THA and 3 g of methyl ethyl ketone was refluxed, and samples were taken at 0, 1, 2, 3, and 5 hours. The 0 hr. sample was obtained after distillation of the small amount of water which formed by the reaction of 6-aminocapronitrile and methyl ethyl ketone, and the pot temperature rose to the boiling point of 6-aminocapronitrile. THA at these times measured, 0.1, 0.1, 0.12, 0.11, 0.12%.

Example 9—Acetophenone

A mixture of 97 g of 6-aminocapronitrile containing 0.32% THA and 3 g of acetophenone was refluxed, and samples were taken at 0, 1, 2, 3, and 5 hours. The 0 hr. sample was obtained after distillation of the small amount of water which formed by the reaction of 6-aminocapronitrile and acetophenone, and the pot temperature rose to the boiling point of 6-aminocapronitrile. THA at these times measured, 0.18, 0.16, 0.16, 0.14, 0.14%.

Example 10—Cyclohexanone

A mixture of 97 g of 6-aminocapronitrile containing 0.32% THA and 3 g of cyclohexanone was refluxed, and samples were taken at 0, 1, 2, 3, and 5 hours. The 0 hr. sample was obtained after distillation of the small amount of water which formed by the reaction of 6-aminocapronitrile and cyclohexanone, and the pot temperature rose to the boiling point of 6-aminocapronitrile. THA at these times measured, 0.11, 0.09, 0.05, 0.03, 0.02%.

Example 11—Hexanal

A mixture of 97 g of 6-aminocapronitrile containing 0.32% THA and 3 g of hexanal was refluxed, and samples were taken at 0, 1, 3, 5, and 7 hours. The 0 hr. sample was obtained after distillation of the small amount of water which formed by the reaction of 6-aminocapronitrile and hexanal, and the pot temperature rose to the boiling point of 6-aminocapronitrile. THA at these times measured, 0.2, 0.14, 0.14, 0.13%.

Example 12—5-formylvaleronitrile

A mixture of 97 g of 6-aminocapronitrile containing 0.32% THA and 3 g of 5-formylvaleronitrile was refluxed, and samples were taken at 0, 1, 2, 3, and 5 hours. The 0 hr. sample was obtained after distillation of the small amount of water which formed by the reaction of 6-aminocapronitrile and 5-formylvaleronitrile, and the pot temperature rose to the boiling point of 6-aminocapronitrile. THA at these times measured, 0.12, 0.07, 0.06, 0.04, 0.02%.

Example 13—5-formylvaleronitrile Generated by Treating Hot 6-ACN with Air

Carbon dioxide-free air was passed over 50 grams of hot (160 degree C.) 6-ACN containing 2500 ppm THA for one hour. This generated 1.7% of the 6-ACN imine of 5-formylvaleronitrile. The solution was then heated to reflux (235 degrees C.). After one hour as reflux, the 6-ACN contained 320 ppm of THA. After 2 hours at reflux, the 6-ACN contained 90 ppm THA. Distillation of the 6-ACN at 0.3 mm Hg, gave a distillate containing only 70 ppm THA.

I claim:

1. A process for the recovery of 6-aminocapronitrile from a mixture containing 6-aminocapronitrile and tetrahydroazepine which comprises (a) heating said mixture at a temperature about 235 degrees C. to convert tetrahydroazepine to higher boiling compounds, and (b) then distilling the 6-aminocapronitrile from the resulting mixture.

2. The process of claim 1 in which an organic carbonyl compound is in the initial mixture to increase the speed at which the tetrahydroazepine is converted.

3. The process of claim 2, in which the organic carbonyl compound is a ketone or an aldehyde.

4. The process of claim 3 in which the amount of organic compound is from 0.1 to 10% by weight of the initial mixture.

5. The process of claim 4 in which the compound is cyclopentanone.

6. The process of claim 5 in which the compound is 5-formylvaleronitrile.

7. The process of claim 2 in which the compound is 2-methyl cyclopentanone.

8. The process of claim 2 in which the initial mixture contains the imines of cyclopentanone and 2-methyl cyclopentanone.

* * * * *